United States Patent [19]

Okamoto et al.

[11] 4,055,636

[45] Oct. 25, 1977

[54] N²-ALKOXYNAPHTHALENESULFONYL-L-ARGININAMIDES AND THE PHARMACEUTICALLY ACCEPTABLE SALTS THEREOF

[75] Inventors: Shosuke Okamoto, Kobe; Ryoji Kikumoto; Kazuo Ohkubo, both of Tokyo; Tohru Tezuka, Yokohama; Shinji Tonomura, Tokyo; Yoshikuni Tamao, Yokohama; Akiko Hijikata, Kobe, all of Japan

[73] Assignees: Mitsubishi Chemical Industries Ltd., Tokyo; Shosuke Okamoto, Kobe, both of Japan

[21] Appl. No.: 638,985

[22] Filed: Dec. 9, 1975

Related U.S. Application Data

[60] Continuation-in-part of Ser. No. 671,436, March 29, 1976, which is a division of Ser. No. 622,390, Oct. 14, 1975, abandoned.

[51] Int. Cl.² .................... A61K 37/00; C07C 103/52
[52] U.S. Cl. ........................ 424/177; 260/518 R; 260/112.5 R; 424/309; 560/10
[58] Field of Search ........... 260/112.5 R, 470, 518 R; 424/177, 309

[56] References Cited

U.S. PATENT DOCUMENTS 3,622,615  11/1971  Nicolaides et al. .................. 260/470

*Primary Examiner*—Delbert R. Phillips
*Attorney, Agent, or Firm*—Oblon, Fisher, Spivak, McClelland & Maier

[57] ABSTRACT

N²-alkoxynaphthalenesulfonyl-L-arginiamides and the pharmaceutically acceptable salts thereof have been found to be effective as pharmaceutical agents for the inhibition and suppression of thrombosis, and are prepared by reacting N²-alkoxynaphthalenesulfonyl-L-arginyl halide with a secondary amine.

10 Claims, No Drawings

N²-ALKOXYNAPHTHALENESULFONYL-L-ARGININAMIDES AND THE PHARMACEUTICALLY ACCEPTABLE SALTS THEREOF

CROSS REFERENCE TO RELATED APPLICATIONS

This application is a continuation in part of application Ser. No. 671,436 Mar. 29, 1976, which in turn was a divisional of application Ser. No. 622,390 filed Oct. 14, 1975 now abandoned.

BACKGROUND OF THE INVENTION

1. Field of the Invention

This invention relates to the discovery of certain new and useful N²-alkoxynaphthalenesulfonyl-L-argininamides and the pharmaceutically acceptable salts thereof, which are of especial value in view of their outstanding antithrombotic properties and low toxicities.

2. Description of the Prior Art

In the past, there have been many attempts to obtain new and improved agents for the treatment of thrombosis. The N²-(p-tolylsulfonyl)-L-arginine esters have been found to be one type of agent which can be used and these have been found to be effective in dissolving blood clots. (U.S. Pat. No. 3,622,615, issued Nov. 23, 1971)

One family of compounds which have been found to be particularly useful as highly specific inhibitors of thrombin for the control of thrombosis is the N²-dansyl-L-arginine ester or amide. (Our pending U.S. application Ser. No. 496,939, filed Aug. 13, 1974 now U.S. Pat. No. 3,978,045)

However, there is a continuing need for a highly specific inhibitor or thrombin for the control of thrombosis, which exhibits lower toxicity.

SUMMARY OF THE INVENTION

It has now been discovered that N²-alkoxynaphthalenesulfonyl-L-argininamides exhibit antithrombotic activity and even lower toxicity levels at the same relative potencies, as compared with the N²-dansyl-L-arginine ester or amide.

The compounds of this invention can be represented by the formula (I):

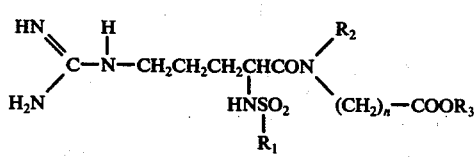

wherein $R_1$ is naphthyl substituted with at least one $C_1$–$C_5$ alkoxy $R_2$ is $C_2$–$C_{10}$ alkyl or $C_2$–$C_{10}$ alkoxyalkyl; $R_3$ is hydrogen or $C_1$–$C_{10}$ alkyl; and $n$ is an integer of 1, 2 or 3.

Also encompassed within this invention are pharmaceutically acceptable salts thereof.

This invention also relates to a method for inhibiting activity and suppressing activation of thrombin into vivo, which comprises introducing into a living body a pharmaceutically effective amount of an N²-alkoxynaphthalenesulfonyl-L-argininamide or the pharmaceutically acceptable salts thereof.

Another aspect of this invention relates to a process for producing N²-alkoxynaphthalenesulfonyl-L-argininamides, which comprises reacting an N²-alkoxynaphthalenesulfonyl-L-arginyl halide with a corresponding secondary amine.

DETAILED DESCRIPTION OF THE PREFERRED EMBODIMENTS

This invention relates to a group of N²-alkoxynaphthalenesulfonyl-L-argininamides of the formula (I):

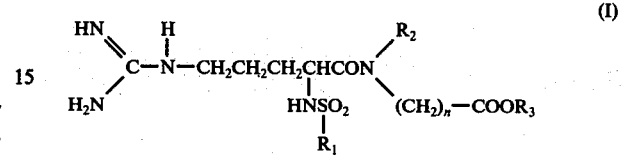

wherein $R_1$ is an alkoxynaphthyl wherein the alkoxy groups have 1–5 (preferably 1–3) carbon atoms, such as methoxy, ethoxy, propoxy, isopropoxy, butoxy, sec-butoxy, tert-butoxy, pentyloxy or the like. Preferred are those naphthyl groups having one or two alkoxy substituents, when two or more alkoxy groups are present, each may be the same of different; $R_2$ is alkyl of 2–10 (preferably 2–6) carbon atoms, such as ethyl, propyl butyl, isobutyl, pentyl, hexyl, octyl, decyl or the like, or alkoxyalkyl of 2–10 (preferably 2–6) carbon atoms, such as methoxymethyl, ethoxymethyl, propoxymethyl, 2-methoxyethyl, 2-ethoxyethyl, 2-propoxyethyl, 3-methoxypropyl, 3-ethoxypropyl, 3-propoxypropyl, 4-methoxybutyl, 4-ethoxybutyl, 4-butoxybutyl, 5-butoxypentyl and the like; $R_3$ is hydrogen or $C_1$–$C_{10}$ alkyl such as methyl, ethyl, propyl, butyl, tert-butyl, hexyl, octyl, decyl or the like; and $n$ is an integer of 1, 2 or 3.

Suitable illustrations of $R_1$ in the above formula (I) are 5-methoxy-1-naphthyl, 6-methoxy-2-naphthyl, 7-methoxy-2-naphthyl, 4,6-dimethoxy-2-naphthyl, 7-methoxy-2-naphthyl, 4,6-dimethoxy-2-naphthyl, 6,7-dimethoxy-2-naphthyl and 6,7-diethoxy-2-naphthyl.

Suitable $R_2$ groups in the above formula (I) are propyl, butyl, isobutyl, pentyl, hexyl, octyl, 2-methoxyethyl, 2-ethoxyethyl and 3-methoxypropyl.

Suitable —$(CH_2)_n$—$COOR_3$ groups in the above formula (I) are carboxymethyl, 2-carboxyethyl, 3-carboxypropyl, ethoxycarbonylmethyl, tert-butoxycarbonylmethyl, 2-ethoxycarbonylethyl, 2-tert-butoxycarbonylethyl, and 3-tert-butoxycarbonylpropyl.

Illustrative of suitable N²-alkoxynaphthalenesulfonyl-L-arginamides of sufficient activity of this invention are the following:

N²-(6,7-dimethoxy-2-naphthalenesulfonyl)-L-arginyl-N-propylglycine

N²-(6,7-dimethoxy-2-naphthalenesulfonyl)-L-arginyl-N-propylglycine tert-butyl ester N²-(6,7-dimethoxy-2-naphthalenesulfonyl)-L-arginyl-N-butylglycine N²-(6,7-dimethoxy-2-naphthalenesulfonyl)-L-arginyl-N-butylglycine tert-butyl ester N²-(6,7-dimethoxy-2-naphthalenesulfonyl)-L-arginyl-N-isobutylglycine N²-(6,7-dimethoxy-2-naphthalenesulfonyl)-L-arginyl-N-isobutylglycine tert-butyl ester N²-(6,7-dimethoxy-2-naphthalenesulfonyl)-L-arginyl-N-pentylglycine N²-(6,7-dimethoxy-2-naphthalenesulfonyl)-L-arginyl-N-pentylglycine tert-butyl ester
N²-(6,7-dimethoxy-2-naphthalenesulfonyl)-L-arginyl-N-hexylglycine
N²-(6,7-dimethoxy-2-naphthalenesulfonyl)-L-arginyl-N-hexylglycine tert-butyl ester
N²-(6,7-dimethoxy-2-naphthalenesulfonyl)-L-arginyl-N-octylglycine
N²-(6,7-dimethoxy-2-naphthalenesulfonyl)-L-arginyl-N-octylglycine tert-butyl ester
N²-(6,7-dimethoxy-2-naphthalenesulfonyl)-L-arginyl-N-(2-methoxyethyl)glycine
N²-(6,7-dimethoxy-2-naphthalenesulfonyl)-L-arginyl-N-(2-methoxyethyl)glycine ethyl ester
N²-(6,7-dimethoxy-2-naphthalenesulfonyl)-L-arginyl-N-(2-methoxyethyl)-β-alanine
N²-(6,7-dimethoxy-2-naphthalenesulfonyl)-L-arginyl-N-(2-methoxyethyl)-β-alanine ethyl ester
N²-(6,7-dimethoxy-2-naphthalenesulfonyl)-N-(2-methoxyethyl)-N-(3-carboxypropyl)-L-argininamide
N²-(6,7-dimethoxy-2-naphthalenesulfonyl)-N-(2-methoxyethyl)-N-(3-tert-butoxycarbonylpropyl)-L-argininamide
N²(6,7-dimethoxy-2-naphthalenesulfonyl)-N-(3-methoxypropyl)glycine
N²-(6,7-dimethoxy-2-naphthalenesulfonyl)-N-(3-methoxypropyl)glycine tert-butyl ester
N²-(6,7-dimethoxy-2-naphthalenesulfonyl)-L-arginyll-N-(2-ethoxyethyl)-β-alanine
N²-(6,7-dimethoxy-2-naphthalenesulfonyl)-L-arginyl-N-(2-ethoxyethyl)-β-alanine tert-butyl ester
N²-(4,6-dimethoxy-2-naphthalenesulfonyl)-L-arginyl-N-(2-methoxyethyl)glycine
N²-(4,6-dimethoxy-2-naphthalenesulfonyl)-L-arginyl-N-(2-methoxyethyl)glycine ethyl ester
N²-(4,6-dimethoxy-2-naphthalenesulfonyl)-L-arginyl-N-butylglycine
N²-(4,6-dimethoxy-2-naphthalenesulfonyl)-L-arginyl-N-butylglycine tert-butyl ester
N²-(6,7-diethoxy-2-naphthalenesulfonyl)-L-arginyl-N-(2-methoxyethyl)glycine
N²-(6,7-diethoxy-2-naphthalenesulfonyl)-L-arginyl-N-(2-methoxyethyl)glycine tert-butyl ester
N²-(6,7-diethoxy-2-naphthalenesulfonyl)-L-arginyl-N-butylglycine
N²-(6,7-diethoxy-2-naphthalenesulfonyl)-L-arginyl-N-butylglycine tert-butyl ester
N²-(6-methoxy-2-naphthalenesulfonyl)-L-arginyl-N-butylglycine
N²-(6-methoxy-2-naphthalenesulfonyl)-L-arginyl-N-butylglycine tert-butyl ester
N²-(6-methoxy-2-naphthalenesulfonyl)-L-arginyl-N-(2-methoxyethyl)glycine
N²-(6-methoxy-2-naphthalenesulfonyl)-L-arginyl-N-(2-methoxyethyl)glycine tert-butyl ester
N²-(7-methoxy-2-naphthalenesulfonyl)-L-arginyl-N-(2-methoxyethyl)glycine
N²-(7-methoxy-2-naphthalenesulfonyl)-L-arginyl-N-(2-methoxyethyl)glycine ethyl ester
N²-(7-methoxy-2-naphthalenesulfonyl)-L-arginyl-N-propylglycine
N²-(7-methoxy-2-naphthalenesulfonyl)-L-arginyl-N-propylglycine tert-butyl ester
N²-(7-methoxy-2-naphthalenesulfonyl)-L-arginyl-N-butylglycine
N²-(7-methoxy-2-naphthalenesulfonyl)-L-arginyl-N-butylglycine tert-butyl ester
N²-(7-methoxy-2-naphthalenesulfonyl)-L-arginyl-N-pentylglycine
N²-(7-methoxy-2-naphthalenesulfonyl)-L-arginyl-N-pentylglycine tert-butyl ester
N²-(5-methoxy-1-naphthalenesulfonyl)-L-arginyl-N-(2-methoxyethyl)glycine
N²-(5-methoxy-1-naphthalenesulfonyl)-L-arginyl-N-(2-methoxyethyl)glycine tert-butyl ester
N²-(5-methoxy-1-naphthalenesulfonyl)-L-arginyl-N-butylglycine
N²-(5-methoxy-1-naphthalenesulfonyl)-L-arginyl-N-butylglycine tert-butyl ester
N²-(5-methoxy-1-naphthalenesulfonyl)-L-arginyl-N-(2-methoxyethyl)-β-alanine
N²-(5-methoxy-1-naphthalenesulfonyl)-L-arginyl-n-(2-methoxyethyl)-β-alanine tert-butyl ester The pharmaceutically acceptable salts of the above compounds are of course also included within the scope of this invention.

The above compounds are intended only to illustrate the variety of structures which can be used in the process of this invention, and the above listing is not to be construed as limiting the scope of the invention.

These typical compounds are highly potent in their antithrombotic activity.

For the preparation of the compounds of this invention, various methods can be employed depending upon the particular starting materials and/or intermediates involved. Successful preparation of these compounds is possible by way of several synthetic routes which are outlined below.

a. Condensation of an L-argininamide with an alkoxynaphthalenesulfonyl halide

This process may be illustrated as follows:

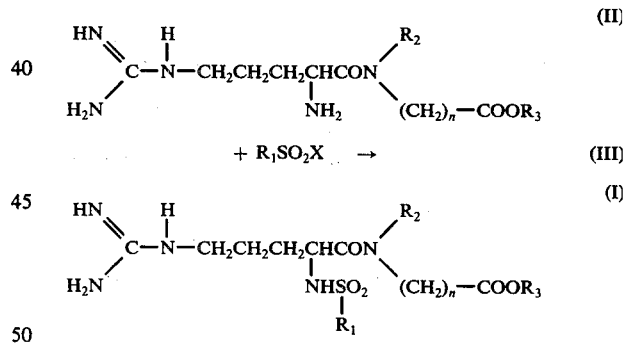

In the above formulas, $R_1$, $R_2$, $R_3$ and $n$ are as defined herein above, and X is halogen.

The N²-alkoxynaphthalenesulfonyl-L-argininamide (I) is prepared by the condensation of an L-argininamide (II) with a substantially equimolar amount of an alkoxynaphthalenesulfonyl halide (III), preferably a chloride.

The condensation reaction is generally effected in a suitable reaction-inert solvent in the presence of an excess of a base, such as an organic base (triethylamine, pyridine) or a solution of an inorganic base (sodium hydroxide, potassium carbonate), at a temperature of 0° C to the boiling temperature of the solvent for a period of 10 minutes to 15 hours.

The preferred solvents for the condensation include benzene-diethyl ether, diethyl ether-water and dioxane-water.

After the reaction is complete, the formed salt is extracted with water, and the solvent is removed by such standard means as evaporation under reduced pressure to give the N²-alkoxynaphthalenesulfonyl-L-argininamide (I), which can be purified by trituration of recrystallization from a suitable solvent, such as diethyl ether-tetrahydrofuran, diethyl ether-methanol and water-methanol, or may be chromatographed on silica gel.

The L-argininamides (II) starting materials required for the condensation reaction can be prepared by protecting in guanidino and α-amino groups of the L-arginine via nitration, acetylation, formylation, phthaloylation, trifluoroacetylation, p-methoxybenzyloxycarbonylation, benzoylation, benzyloxycarbonylation, tert-butoxycarbonylation or tritylation and then condensing the formed N$^G$-substituted-N²-substituted-L-arginine with a corresponding secondary amine by such a conventional process as the acid chloride method, azide method, mixed anhydride method, activated ester method or carbodiimide method, and thereafter selectively removing the protective group.

b. Removal of the N$^G$-substituent from an N$^G$-substituted-N²-alkoxynaphthenesulfonyl-L-argininamide This process may be illustrated as follows:

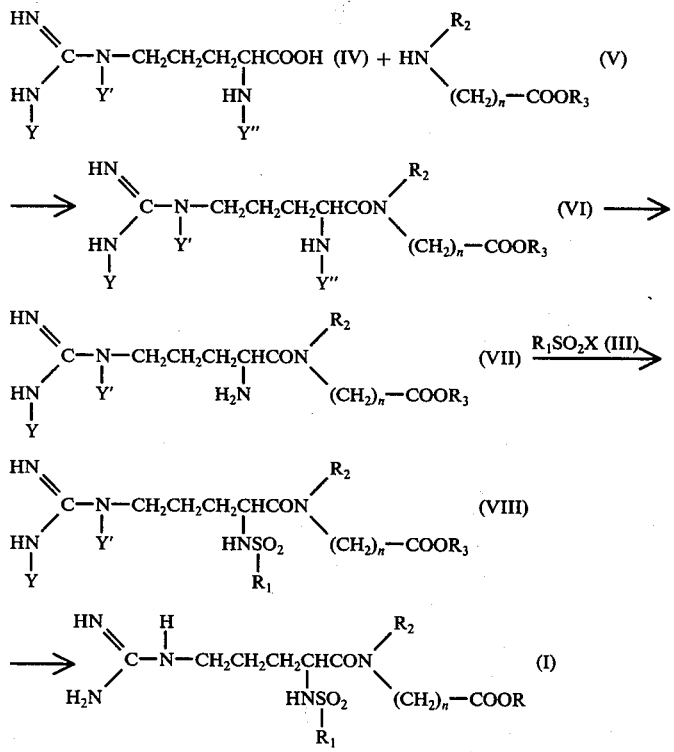

In the above formulas, $R_1$, $R_2$, $R_3$, X and n are as defined herein above; Y" is a protective group for the amino group, such as benzyloxycarbonyl or tertbutyoxycarbonyl; and Y and Y' are hydrogen and protective groups for the guanidino group, such as nitro, tosyl, trityl, oxycarbonyl or the like. At least one of Y and Y' is a protective group for the guanidino group.

The N²-alkoxynapthalene sulfonyl-L-argininamide (I) is prepared by removing the N$^G$-substituent from an N$^G$-substituted-N²-alkoxynaphthalenesulfonyl-L-argininamide (VIII) by means of acidolysis or hydrogenolysis.

The acidolysis is generally effected by contacting the N$^G$-substituted-N²-alkoxynaphthalenesulfonyl-L-argininamide (VIII) and an excess of an acid such as hydrogen fluoride, hydrogen chloride, hydrogen bromide or trifluoroacetic acid, without a solvent or in a solvent, such as an ether (tetrahydrofuran, dioxane), an alcohol (methanol, ethanol) or acetic acid at a temperature of −10° C to 100° C, and preferably at room temperature for a period of 30 minutes to 24 hours.

The products are isolated by evaporation of the solvent and the excess acid, or by trituration with a suitable solvent followed by filtration and drying.

Because of the use of the excess acid, the products are generally the acid addition salts of the N²-alkoxynaphthalenesulfonyl-L-argininamides (I), which can be easily converted to a free amide by neutralization.

The removal of the nitro group and the oxycarbonyl group, e.g., benzyloxycarbonyl, p-nitrobenzyloxycarbonyl, is readily accomplished by the hydrogenolysis.

The hydrogenolysis is effected in a reaction-inert solvent, e.g., methanol, ethanol, tetrahydrofuran or dioxane, in the presence of a hydrogen-activating catalyst, e.g., Raney nickel, palladium, or platinum, in a hydrogen atmosphere at a temperature of 0° C to the boiling temperature of the solvent for a period of 2 hours to 120 hours.

The hydrogen pressure is not critical, and atmospheric pressure is sufficient.

The N²-alkoxynaphthalenesulfonyl-L-argininamide (I) are isolated by filtration of the catalyst followed by evaporation of the solvent.

The N²-alkoxynaphthalenesulfonyl-L-argininamides can be purified in the same manner as described above.

The N$^G$-substituted-N²-alkoxynaphthalenesulfonyl-L-argininamides (VIII) starting materials can be prepared by condensing an N$^G$-substituted-N²-substituted L-arginine (IV) (generally the N²-substituent is a protective group for the amino group, such as benzyloxycarbonyl, tert-butoxycarbonyl, or the like) and a corresponding secondary amine (V) via the azide method, mixed anhydride method, activated ester method, carbodiimido method or the like, selectively removing only the N²-substituent of an N^G-substitited-N²-substituted L-argininamide (VI) by means of catalytic hydrogenolysis or acidolysis, and then condensing the thus obtained N^G-substituted-L-argininamide (VII) with an alkoxynaphthalenesulfonyl halide (III), preferably a chloride in the presence of a base in a solvent. These reaction conditions are as described above in the condensation of an L-argininamide with an alkoxynaphthalenesulfonyl halide, and the removal of the N^G-substituent from an N^G-substituted-N²-alkoxynaphthalenesulfinyl-L-argininamide c. Condensation of an N²-alkoxynaphthalenesulfonyl-L-arginyl halide with an amine This process may be illustrated as follows:

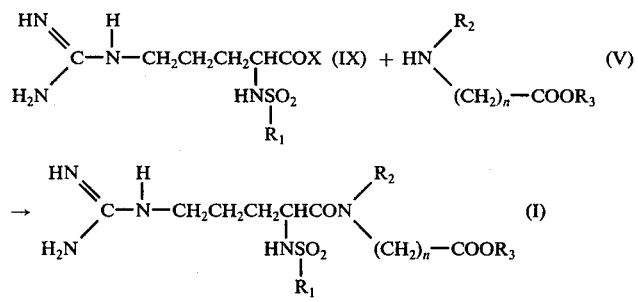

In the above formulas, $R_1, R_2, R_3, X$ and $n$ are as defined herein above.

The N²-alkoxynaphthalenesulfonyl-L-arginamide (I) is prepared by the condensation of an N²-alkoxynaphthalenesulfonyl-L-arginyl halide (IX), preferably a chloride with at least an equimolar amount of a secondary amine (V).

The condensation reaction can be carried out without an added solvent. However, satisfactory results will be obtained with the use of a solvent such as basic solvents (dimethylformamide, dimethylacetamide, etc.) or halogenated solvents (chloroform, dichloromethane, etc.).

The amount of the solvent to be used is not critical and may vary from about 5 to 100 times the weight of the N²-alkoxynaphthalenesulfonyl-L-arginylhalide (IX).

Preferred condensation reaction temperatures are in the range of from $-10°$ C to room temperature. The reaction time is not critical, but varies with the secondary amine (V) employed. In general, a period of from 5 minutes to 10 hours is operable.

The obtained N²-alkoxynaphthalensulfonyl-L-argininamide can be isolated and purified in the same manner as described above.

The N²-alkoxynaphthalenesulfonyl-L-arginyl halide (IX) starting materials required for the condensation reaction can be prepared by reacting an N²-alkoxynaphthalenesulfonyl-L-arginine with at least an equimolar amount of halogenating agent such as thionyl chloride, phosphorus oxychloride, phosphorus trichloride, phosphorus pentachloride or phosphorus tribromide. The halogenation can be carried out with or without an added solvent.

The preferred solvents are chlorinated hydrocarbons such as chloroform and dichloromethane, and ethers such as tetrahydrofuran and dioxane.

The amount of the solvent to be used is not critical and may vary from about 5 to 100 times the weight of the N²-alkoxynaphthalenesulfonyl-L-arginine. Preferred reaction temperatures are in the range of $-10°$ C to room temperature. The reaction time is not critical, but varies with the halogenating agent and reaction temperature. In general, a period of 15 minutes to 5 hours is operable.

d. Guanidylation of an N²-alkoxynaphthalenesulfonyl-L-ornithinamide or an acid addition salt thereof This process may be illustrated as follows:

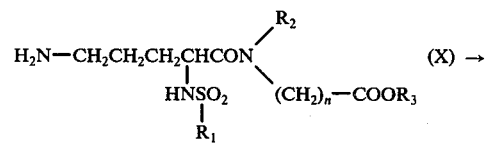

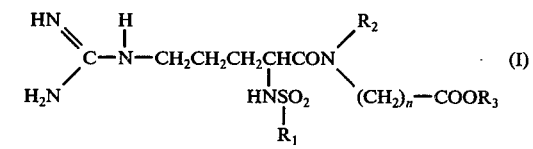

In the above formulas, $R_1$, $R_2$, $R_3$ and $n$ are as defined herein above.

The N²-alkoxynaphthalenesulfonyl-L-argininamide (I) is prepared by guanidylating an N²-alkoxynaphthalenesulfonyl-L-ornithinamide (X) with an ordinary guanidylating agents such as an O-alkylisourea, S-alkylisothiourea, 1-guanyl-3,5-dimethylpyrazole or carbodiimide. The preferred guanidylating agents are the O-alkylisourea and the S-alkylisothiourea.

The guanidylation of the N²-alkoxynaphthalenesulfonyl-L-ornithinamide (X) with the O-alkylisourea or S-alkylisothiourea is generally effected in a solvent in the presence of a base at a temperature of from 0° C to the boiling temperature of the solvent for a period of from 30 minutes to 50 hours.

Examples of the preferred base are triethylamine, pyridine, sodium hydroxide and sodium methoxide.

The base is used in an amount of 0.01 to 0.1 equivalent to the N²-alkoxynaphthalenesulfonyl-L-ornithinamide.

Examples of the preferred solvent are water, water-ethanol and water-dioxane.

After the reaction is complete, the N²-alkoxynaphthalenesulfonyl-L-argininamide (I) is isolated by evaporation of the solvent followed by removal of the excess base and the formed salt by a water wash.

It is well recognized in the art that an ester derivative of the N²-alkoxynaphthalenesulfonyl-L-argininamide argininamide (I) wherein $R_3$ is alkyl, can be prepared from a carboxylic acid derivative of the N²-alkoxynaphthalenesulfonyl-L-argininamide wherein $R_3$ is hydrogen, by the conventional esterification methods well known to those skilled in the art. It is also well recognized in the art that the carboxylic acid derivative can be prepared from the ester derivative by the conventional hydrolysis or acidolysis methods. The conditions under which esterification, hydrolysis or acidolysis would be carried out will be each apparent to those skilled in the art.

The $N^2$-alkoxynaphthalenesulfonyl-L-argininamide (I) of this invention forms acid addition salts with any of a variety of inorganic and organic acids. Some of the $N^2$-alkoxynaphthalenesulfonyl-L-argininamide containing a free carboxy group, wherein $R_3$ is hydrogen, forms salts with any of a variety of inorganic and organic bases. The product of the reactions described above can be isolated in the free form or in the form of salts. In addition, the product can be obtained as pharmaceutically acceptable acid addition salts by reacting one of the free bases with an acid, such as hydrochloric, hydrobromic, hydroiodic, nitric, sulfuric, phosphoric, acetic, citric, maleic, succinic, lactic, tartaric, gluconic, benzoic, methanesulfonic, ethanesulfonic, benzenesulfonic, p-toluenesulfonic acid or the like. In a similar manner, the product can be obtained as pharmaceutically acceptable salts by reacting one of the free carboxylic acids with an base, such as sodium hydroxide, potassium hydroxide, ammonium hydroxide, triethylamine, procaine, dibenzylamine, 1-ephenemine, N,N'-dibenzylethylendiamine, N-ethylpiperidine or the like.

Likewise, treatment of the salts with a base or acid results in a regeneration of the free amide.

As stated above, the $N^2$-alkoxynaphthalenesulfonyl-L-argininamides, and the salts thereof of this invention are characterized by highly specific inhibitory activity against thrombin as well as their substantial lack of toxicity, and therefore these compounds are useful in the determination of thrombin in blood as diagnostic reagents, and/or for the medical control or prevention of thrombosis.

The antithrombotic activities of the $N^2$-alkoxynaphthalenesulfonyl-L-argininamide of this invention were compared with that of a known antithrombotic agent, $N^2$-(p-tolylsulfonyl)-L-arginine methyl ester, by determining the fibrinogen coagulation time. The measurement of the fibrinogen coagulation time was conducted as follows:

An 0.8 ml aliquot of a fibrinogen solution, which had been prepared by dissolving 150 mg of bovine fibrinogen (Cohn fraction I) supplied by Armour Inc. in 40 ml of a borate saline buffer (pH 7.4), was mixed with 0.1 ml of a borate saline buffer, pH 7.4, (control) or a sample solution in the same buffer, and 0.1 ml of a thrombin solution (5 units/ml) supplied by Mochida Pharmaceutical Co., Ltd. was added to the solutions in an ice bath. Immediately after mixing, the reaction mixture was transferred from the ice bath to a bath maintained at 25° C. Coagulation times were taken as the period between the time of transference to the 25° C bath and the time of the first appearance of fibrin threads. In the cases where no drug samples were added, the coagulation time was 50–55 seconds.

The experimental results are summarized in Table 1. The term "concentration required to prolong the coagulation time by a factor of two" is the concentration of an active ingredient required to prolong the normal coagulation time 50–55 seconds to 100–110 seconds.

The concentration required to prolong the coagulation time by a factor of two for the known antithrombotic agent, $N^2$-(p-tolylsulfonyl)-L-arginine methyl ester, was 1,1000 μm.

The inhibotors are shown in Table 1 by indicating $R_1$, $R_2$, $R_3$ and n in the formula (I) and the addition moiety.

When a solution containing an $N^2$-alkoxynaphthalenesulfonyl-L-argininamide of this invention was administered intravenously into animal bodies, the high antithrombotic activity in the circulating blood was maintained for from one to three hours. The halflife for decay of the antithrombotic compounds of this invention in circulating blood was shown to be approximately 60 minutes; the physiological conditions of the host animals (rat, rabbit, dog and chimpanzee) were well maintained. The experimental decrease of fibrinogen in animals caused by infusion of thrombin was satisfactorily controlled by simultaneous infusion of the compounds of this invention.

The acute toxicity values ($LD_{50}$) determined by intraperitoneal administration of substances of formula (I) in mice (male, 20 g) range from about 1,000 to 10,000 milligrams per kilogram of body weight. Representative $LD_{50}$ values, for example, for $N^2$-(6,7-dimethoxy-2-naphthalenesulfonyl)-L-arginyl-N-(2-methoxyethyl)glycine, $N^2$-(6,7-dimethoxy-2-naphthalenesulfonyl)-L-arginyl-N-(2-ethoxyethyl)-β-alanine, $N^2$-(4,6-dimethoxy-2-naphthalenesulfonyl)-L-arginyl-N-(2-methoxyethyl)glycine, $N^2$-(7-methoxy-2-naphthalenesulfonyl)-L-arginyl-N-(2-methoxyethyl)glycine are 1,900–2,400, 660–1,000, 660–1,000, 2,000 milligrams per kilogram, respectively.

On the other hand, $LD_{50}$ values for $N^2$-dansyl-N-butyl-L-argininamide and $N^2$-dansyl-N-methyl-N-butyl-L-argininamide are 75 and 70 milligrams per kilogram, respectively.

The therapeutic agents of this invention may be administered alone or in combination with pharmaceutically acceptable carriers, the proportion of which is determined by the solubility and chemical nature of the compound, chosen route of administration and standard pharmaceutical practice. For example, the compounds may be injected parenterally, that is, intramuscularly, intravenously or subcutaneously. For parenteral administration, the compounds may be used in the form of sterile solutions containing other solutes, for example, sufficient saline or glucose to make the solution isotonic. The compounds may be administered orally in the form of tablets, capsules, or granules containing suitable excipients such as starch, lactose, white sugar and the like. The compounds may be administered sublingually in the form of troches or lozenges in which each active ingredient is mixed with sugar or corn syrups, flavoring agents and dyes, and then dehydrated sufficiently to make the mixture suitable for pressing into solid form. The compounds may be administered orally in the form of solutions which may contain coloring and flavoring agents.

Physicians will determine the dosage of the present therapeutic agents which will be most suitable, and dosages vary with the mode of administration and the particular compound chosen. In addition, the dosage will vary with the particular patient under treatment.

When the composition is administered orally, a larger quantity of the active agent will be required to produce the same effect as caused with a smaller quantity given parenterally. The therapeutic dosage is generally 10–50 mg/kg of active ingreidnet parenterally, 10–500 mg/kg orally per day.

Having generally described the invention, a more complete understanding can be obtained by reference to certain specific examples, which are included for purposes of illustration only and are not intended to be limiting unless otherwise specified.

EXAMPLE 1

N[2]-(4,6-dimethoxy-2-naphthalenesulfonyl)-L-arginyl-N-(2-methoxyethyl)glycine

A.

N[2]-(4,6-dimethoxy-2-naphthalenesulfonyl)-L-arginyl-N-(2-methoxyethyl)glycine ethyl ester To a well stirred solution of 2.00 g of L-arginyl-N-(2-methoxyethyl)glycine ethyl ester and 1.04 g of $K_2CO_3$ in 20 ml of water and 10 ml of dioxane was added dropwise a solution of 2.17 g of 4,6-dimethoxy2-naphthalenesulfonyl chloride in 30 ml of dioxane over a period of 30 minutes while maintaining the temperature at 0° C. The reaction mixture was stirred for an additional 5 hours at room temperature. At the end of this period, the solvent was evaporated and the residue taken up in 50 ml of chloroform. The chloroform solution was filtered to remove the insoluble material and dried over anhydrous sodium sulfate. Addition of 150 ml of diethyl ether to the chloroform solution resulted in a precipitate which was separated by decantation and purified by reprecipitation with ethanol-diethyl ether to give 2.58 g (72 percent) of N[2]-(4,6-dimethoxy-2-naphthalenesulfonyl)-L-arginyl-N-(2-methoxyethyl)glycine ethyl ester.

For analysis of the product, a portion of the product was converted to the flavianate; M.P. 225°–227° C, I.R. (KBr): 3,375, 3,200, 1.742 cm$^{-1}$.

Analysis — Calcd. for $C_{25}H_{37}N_5O_8S \cdot C_{10}H_6 N_2O_8S$ (percent): C, 47.67; H, 4.92; N, 11.12. Found (percent): C, 47.62; H, 4.84; N, 11.18.

B.

N[2]-(4,6-dimethoxy-2-naphthalenesufonyl)-L-arginyl-N-(2-methoxyethyl)glycine

A solution of 2.5 g of N[2]-(4,6-dimethoxy-2-naphthalenesulfonyl)-L-arginyl-N-(2-methoxyethyl)glycine ethyl ester in 5 ml of ethanol and 7 ml of 1N NaOH solution was stirred for 30 hours at room temperature. At the end of this period, the solution was concentrated to 5 ml, chromatographed on 80 ml of Daiaion ® Sk 102 ion exchange resin (200–300 mesh, H+form, manufactured by Mitsubishi Chemical Industries Limited) packed in water, washed with water, and eluted with 3% ammonium hydroxide solution. The fraction eluted from 3% ammonium hydroxide solution was evaporated to dryness, and the residue was purified by reprecipitation with ethanol-diethyl ether to give 1.32 g (72 percent) of N[2]-(4,6-dimthoxy-2-naphthalenesulfonyl)-L-arginyl-N-(2-methoxyethyl)glycine as an amorphous solid, I.R. (KBr): 3,360, 3,180, 1,610 cm$^{-1}$.

Analysis — Calcd. for $C_{23}H_{33}N_5O_8S$ (percent): C, 51.20; H, 6.17; N, 12.98. Found (percent): C, 51.31; H, 6.01; N, 12.67.

EXAMPLE 2

N[2]-(6,7-dimethoxy-2-naphthalenesulfonyl)-L-arginyl-N-(2-methoxyethyl)glycine

To a solution of 3.00 g of N[G]-nitro-N[2]-(6,7-dimethoxy-2-naphthalenesulfonyl)-L-arginyl-N-(2-methoxyethyl)glycine ethyl ester in 50 ml of ethanol and 0.5 ml of acetic acid was added 0.5 g of palladium-black and then the mixture was shaken in a hydrogen atmosphere for 100 hours at room temperature. At the end of this period, the ethanol solution was filtered to remove the catalyst and evaporated to give an oily product. Reprecipitation with ethanoldiethyl ether gave 2.53 g (91%) of N[2]-(6,7-dimethoxy-2-naphthalenesulfonyl)-L-arginyl-N-(2-methoxyethyl)glycine ethyl ester.

For analysis of the product, a portion of the product was coverted to the flavianate; M.P. 185° C, I.R. (KBr): 3,375, 3,200, 1,740 cm$^{-1}$.

Analysis — Calcd. for $C_{25}H_{37}N_5O_8S \cdot C_{10}H_6N_2O_8S$ (percent): C. 47.67; H, 4.92; N, 11.12. Found (percent): C, 47.64; H, 4.81; N, 11.12.

N[2]-(6,7-diemthoxy-2-naphthalenesulfonyl)-L-arginyl-N-(2-methoxyethyl)glycine was prepared by hydrolysis of its ethyl ester in a manner analogous to Example 1.

I.R. (KBr): 3,380, 3,180, 1,630 cm$^{-1}$.

Analysis — Calcd. for $C_{23}H_{33}N_5O_8S$ (percent): C, 51.20; H, 6.17; N, 12.98. Found (percent): C, 50.93; H, 6.02; N, 12.63.

EXAMPLE 3

N[2]-(6,7-dimethoxy-2-nephthalenesulfonyl)-L-arginyl-N-butylglycine

A. N-butylglycine tert-butyl ester

To 36.5 g of butylamine was added with stirring 15.05 g of tert-butyl chloroacetate over a period of 30 minutes, while maintaining the temperature at 30°–70° C. The reaction mixture was held at 70° C for an additional one hour. At the end of this period, the excess butyl amine was evaporated in vacuo, and the residue was taken up in 40 ml of 2N NaOH solution and 50 ml of benzene, transferred into a separatory funnel and well shaken. The benzene solution was separated, washed with water, dried over anhydrous sodium sulfate and filtered. After evaporation of benzene, the residue was distilled under reduced pressure to give 17.0 g (90.9 percent) of N-butylglycine tert-butyl ester, B.P. 76° /4 mmHg.

Analysis — Calcd. for $C_{10}H_{21}NO_2$ (percent): C, 64.13; H, 11.30; N, 7.48. Found (percent): C, 64.03; H, 11.39; N, 7.23.

B. N[2]-(6,7-dimethoxy-2-naphthalensulfonyl)-L-arginyl chloride hydrochloride A suspension of 2.00 g of N[2]-(6,7-dimethoxy-2-naphthalenesulfonyl)-L-arginine in 20 ml of thionyl chloride was stirred for 2 hours at room temperature. Addition of cold dry diethyl ether resulted in a precipitate which was collected by filtration and washed several times with dry diethyl ether to give N[2]-(6,7-dimethoxy-2-naphthalensulfonyl)-L-arginyl chloride hydrochloride.

C.

N[2]-(6,7-dimethoxy-2-naphthalenesulfonyl)-L-arginyl-N-butylglycine tert-butyl ester To a stirred solution of 2.64 g of N-butylglycine tert-butyl ester in 20 ml of chloroform was carefully added N[2]-(6,7-dimethoxy-2-naphthalensulfonyl)-L-arginyl chloride hydrochloride obtained above. The reaction mixture was allowed to stand at room temperature for one hour. At the end of this period, the reaction mixture was washed twice with 20 ml of saturated sodium chloride solution and evaporated to dryness. The residue was triturated with a small amount of water to give a crystalline material. This was collected by filtration and recystallized from ethanol-diethyl ether to give 2.28 g (82 percent) of N[2]-(6,7-dimthoxy-2-naphthalenesulfonyl)-L-arginyl-N-butylglycine tert-butyl ester, M.P. 164°–166° C, I.R. (KBr): 3,390, 3,165, 1,735, 1,370 cm$^{-1}$. Analysis — Calcd. for $C_{28}H_{43}O_7N_5S \cdot \frac{1}{2}H_2SO_3$ (percent): C, 52.98; H, 7.00; N, 11.04. Found (percent): C, 52.69; H, 6.98; N, 10.86.

D.
$N^2$-(6,7-dimethoxy-2-naphthalensulfonyl)-L-arginyl-N-butylglycine

To a solution of 2.00 g of $N^2$-(6,7-dimethoxy-2-naphthalenesulfonyl)-L-arginyl-N-butylglycine tert-butyl ester in 20 ml of chloroform was added 50 ml of 15% HCl-ethyl acetate. The reaction mixture was stirred for 5 hours at room temperature. At the end of this period, the reaction mixture was evaporated to dryness. The residue was washed several times with dry diethyl ether and chromatographed on 80 ml of Daiaion ® SK 102 ion exchange resin (200–300 mesh, H$^+$form, manufactured by Mitsubishi Chemical Industries Limited) packed in water, washed with water and eluted with 3% ammonium hydroxide solution.

The fraction eluted from 3% ammonium hydroxide solution was evaporated to dryness to give 1.43 g (79 percent) of $N^2$-(6,7-dimethoxy-2-naphthalenesulfonyl)-L-arginyl-N-butylglycine as an amorphous solid, I.R. (KBr): 3,360, 3,140, 1,622 cm$^{-1}$. Analysis — Calcd. for $C_{24}H_{35}N_5O_7S$ (percent): C, 53.62; H, 6.56; N, 13.03. Found (percent): C, 53.48; H, 6.43; N, 12.98.

Various other $N^2$-alkoxynaphthalenesulfonyl-L-arginamides or acid addition salts thereof were synthesized in accordance with the procedure of the above examples, and the test results are summarized in Table 1.

TABLE 1

COMPOUND $$HN=C(NH_2)-NH-N(R_1)-SO_2-CH_2CH_2CH(CONHR_2)-(CH_2)_n-COOR_3 \quad (I)$$

| Sample Number | $R_1$ | $R_2$ | $R_3$ | n | Addition Moiety | Concentration Required To Prolong The Coagulation Time By A Factor of Two (μM) | Preparation Process (Ex.No.) | m.p. (°C) | Elemental Analysis Upper: Calculated Lower: Found C | H | N | I.R.(KBr) (cm$^{-1}$) |
|---|---|---|---|---|---|---|---|---|---|---|---|---|
| 1 | OCH₃—[naphthyl]—OCH₃ | —(CH₂)₂CH₃ | H | 1 | — | 8 | 3 | powder | 52.76 / 52.68 | 6.35 / 6.21 | 13.38 / 13.30 | 3,360 3,160 1,620 |
| 2 | " | —(CH₂)₂CH₃ | —C(CH₃)₃ | 1 | ½ H₂SO₃ | | 3 | 134–6 | 52.25 | 6.82 | 11.29 | 3,360 3,180 1,740 1,375 |
| 3 | " | —(CH₂)₃CH₃ | H | 1 | — | 0.3 | 3 | powder | 52.07 / 53.62 | 6.73 / 6.56 | 10.89 / 13.03 | 3,360 3,140 1,622 |
| 4 | " | —(CH₂)₃CH₃ | —C(CH₃)₃ | 1 | ½ H₂SO₃ | | 3 | 164–6 | 53.48 / 52.98 | 6.43 / 7.00 | 12.98 / 11.04 | 3,390 3,165 1,735 1,370 |
| 5 | " | —CH₂CH(CH₃)CH₃ | H | 1 | — | 2 | 3 | powder | 52.69 | 6.98 | 10.86 | 3,360 3,160 1,620 |
| 6 | " | —CH₂CH(CH₃)CH₃ | —C(CH₃)₃ | 1 | ½ H₂SO₃ | | 3 | powder | 53.62 / 53.43 | 6.56 / 6.51 | 13.03 / 13.12 | |
| 7 | " | —(CH₂)₄CH₃ | H | 1 | — | 5 | 3 | powder | 52.98 / 52.59 | 7.00 / 6.79 | 11.04 / 10.89 | 3,390 3,170 1,737 1,370 |
| 8 | " | —(CH₂)₄CH₃ | —C(CH₃)₃ | 1 | ½ H₂SO₃ | | 3 | 195–6 | 54.43 / 54.38 | 6.76 / 6.79 | 12.70 / 12.56 | 3,350 3,180 1,630 |
| 9 | " | —(CH₂)₅CH₃ | H | 1 | — | 1.5 | 3 | powder | 53.69 / 53.40 | 7.15 / 7.12 | 10.80 / 10.56 | 3,380 3,180 1,738 1,375 |
| 10 | " | —(CH₂)₅CH₃ | —C(CH₃)₃ | 1 | ½ H₂SO₃ | | 3 | 198–200 | 55.21 / 54.98 / 54.37 | 6.95 / 7.02 / 7.30 | 12.38 / 12.47 / 10.57 | 3,360 3,200 1,622 3,360 3,160 1,730 |
| 11 | " | —(CH₂)₇CH₃ | H | 1 | — | | 3 | powder | 54.30 / 56.64 | 7.27 / 7.30 | 10.36 / 11.80 | 3,368 3,360 3,180 |
| 12 | " | —(CH₂)₇CH₃ | —C(CH₃)₃ | 1 | ½ H₂SO₃ | | 3 | 172–174 | 56.41 / 55.64 | 7.17 / 7.59 | 11.51 / 10.14 | 1,620 3,380 |

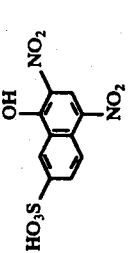

TABLE 1-continued

COMPOUND $$HN\diagdown C-N-CH_2CH_2CH_2CHCON\diagdown R_2 \quad (CH_2)_n-COOR_3 \quad (I)$$
$$H_2N / \quad H \quad H-N-SO_2 \quad R_1$$

| Sample Number | R₁ | R₂ | R₃ | n | Addition Moiety | Concentration Required To Prolong The Coagulation Time By A Factor of Two (μM) | Preparation Process (Ex.No.) | m.p. (°C) | Elemental Analysis Upper: Calculated Lower: Found | | | I.R.(KBr) (cm⁻¹) |
|---|---|---|---|---|---|---|---|---|---|---|---|---|
| | | | | | | | | | C | H | N | |
| 23 | [2,5-dimethoxy-7-methyl-naphthyl, OCH₃, OCH₃] | —CH₂CH₂OCH₃ | H | 1 | — | 4 | 1 | powder | 51.20 51.31 | 6.17 6.01 | 12.98 12.67 | 3,360 3,180 1,610 |
| 24 | " | —CH₂CH₂OCH₃ | —C₂H₅ | 1 | [naphthol disulfonic/nitro structure: HO₃S, OH, NO₂, NO₂] | | 1 | 225–7 | 47.67 47.62 | 4.92 4.84 | 11.12 11.18 | 3,375 3,200 1,742 |
| 25 | " | —(CH₂)₃—CH₃ | H | 1 | — | 2 | 3 | powder | 53.62 53.58 | 6.56 6.48 | 13.03 12.94 | 3,380 3,200 1,630 |
| 26 | " | —(CH₂)₃—CH₃ | —C(CH₃)₃ | 1 | ½H₂SO₄ | | 3 | 224 | 52.98 52.73 | 7.00 7.00 | 11.04 10.82 | 3,360 3,160 1,740 1,370 |
| 27 | [2,3-diethoxy-7-methyl-naphthyl, OC₂H₅, OC₂H₅] | —CH₂CH₂OCH₃ | H | 1 | — | 15 | 3 | powder | 52.89 52.77 | 6.57 6.80 | 12.34 12.59 | 3,380 3,200 1,625 |
| 28 | " | —CH₂CH₂OCH₃ | —C(CH₃)₃ | 1 | ½H₂SO₄ | | 3 | powder | 52.39 | 6.97 | 10.54 | 3,370 3,150 1,740 |
| 29 | " | —(CH₂)₃CH₃ | H | 1 | — | | 3 | powder | 52.10 55.20 | 6.84 6.95 | 10.21 12.38 | 3,360 3,150 1,370 |
| 30 | " | —(CH₂)₃CH₃ | —C(CH₃)₃ | 1 | ½H₂SO₄ | | 3 | powder | 55.00 54.36 | 6.81 7.30 | 12.21 10.57 | 3,370 3,200 1,620 1,735 1,370 |
| 31 | [2-methoxy-7-methyl-naphthyl, OCH₃] | —(CH₂)₃CH₃ | H | 1 | — | 0.5 | 2 | powder | 54.25 54.43 54.21 | 7.11 6.55 6.50 | 10.81 13.80 13.79 | 3,360 3,180 1,632 |
| 32 | " | —(CH₂)₃CH₃ | —C(CH₃)₃ | 1 | ½H₂SO₄ | | 3 | powder | 53.63 | 7.00 | 11.58 | 3,380 3,200 1,740 1,370 |
| 33 | " | —CH₂CH₂OCH₃ | H | 1 | — | | 3 | powder | 53.50 51.86 | 6.79 6.13 | 11.40 13.75 | 3,370 3,370 |

TABLE 1-continued

COMPOUND $$HN=C(NH_2)-NH-CH_2CH_2CH_2CHCON(R_1)(R_2) \quad (I)$$
$$H-N-SO_2-(CH_2)_n-COOR_3$$

| Sample Number | $R_1$ | $R_2$ | $R_3$ | n | Addition Moiety | Concentration Required To Prolong The Coagulation Time By A Factor of Two (μM) | Preparation Process (Ex.No.) | m.p. (°C) | Elemental Analysis Upper: Calculated Lower: Found | | | I.R.(KBr) (cm$^{-1}$) |
|---|---|---|---|---|---|---|---|---|---|---|---|---|
| | | | | | | | | | C | H | N | |
| 34 | ″ | $-CH_2CH_2OCH_3$ | $-C(CH_3)_3$ | 1 | ½ $H_2SO_3$ | | 3 | powder | 51.64 / 55.21 | 6.09 / 6.95 | 13.84 / 12.38 | 3,200 / 1,625 / 3,380 / 3,180 / 1,738 / 1,368 |
| 35 | [2-methoxy-6-methylnaphthalenyl] | $-CH_2CH_2OCH_3$ | H | 1 | — | 0.5 | 2 | powder | 55.11 | 6.76 | 12.27 | 3,370 / 3,160 / 1,620 |
| 36 | ″ | $-CH_2CH_2OCH_3$ | $-C_2H_5$ | 1 | [1-hydroxy-2,4-dinitro-7-sulfonaphthalenyl] | | 2 | 158-160 | 51.86 / 51.72 | 6.13 / 6.11 | 13.75 / 13.63 | 3,375 / 3,200 / 1,740 |
| | | | | | | | | | 47.94 / 47.83 | 4.85 / 4.80 | 11.51 / 11.43 | |
| 37 | ″ | $-(CH_2)_2CH_3$ | H | 1 | — | | 3 | powder | 55.53 | 6.33 | 14.19 | 3,375 / 3,150 |
| 38 | ″ | $-(CH_2)_2CH_3$ | $-C(CH_3)_3$ | 1 | ½ $H_2SO_3$ | | 3 | powder | 53.40 / 52.86 | 6.21 / 6.83 | 14.04 / 11.86 | 1,620 / 3,380 / 3,200 / 1,740 / 1,370 |
| 39 | ″ | $-(CH_2)_3CH_3$ | H | 1 | — | 0.5 | 3 | powder | 52.77 | 6.66 | 11.75 | |
| 40 | ″ | $-(CH_2)_3CH_3$ | $-C(CH_3)_3$ | 1 | ½ $H_2SO_3$ | | 3 | 131-137 (dec) | 54.43 / 54.22 | 6.55 / 6.31 | 13.80 / 13.59 | 3,380 / 3,150 / 1,640 |
| 41 | ″ | $-(CH_2)_4CH_3$ | H | 1 | — | | 3 | powder | 53.63 / 53.40 | 7.00 / 7.10 | 11.58 / 11.40 | 3,380 / 3,160 / 1,750 / 1,640 |
| 42 | ″ | $-(CH_2)_4CH_3$ | $-C(CH_3)_3$ | 1 | ½ $H_2SO_3$ | | 3 | 169-175 (dec.) | 55.26 / 55.21 | 6.76 / 6.65 | 13.43 / 13.29 | 3,350 / 1,630 |
| | | | | | | | | | 54.36 / 54.27 | 7.17 / 7.00 | 11.32 / 11.08 | 3,350 / 3,180 / 1,740 / 1,640 |

TABLE 1-continued

COMPOUND $$\begin{array}{c} HN \quad H \\ \| \quad | \\ H_2N-C-N-CH_2CH_2CH_2CHCON \\ \quad\quad\quad\quad\quad\quad\quad\quad | \\ \quad\quad\quad\quad\quad\quad H-N-SO_2 \\ \quad\quad\quad\quad\quad\quad\quad\quad | \\ \quad\quad\quad\quad\quad\quad\quad\quad R_1 \end{array} \begin{array}{c} R_2 \\ | \\ (CH_2)_n-COOR_3 \end{array} \quad (I)$$

| Sample Number | R₁ | R₂ | R₃ | n | Addition Moiety | Concentration Required To Prolong The Coagulation Time By A Factor of Two (μM) | Preparation Process (Ex.No.) | m.p. (°C) | Elemental Analysis Upper: Calculated Lower: Found | | | I.R.(KBr) (cm⁻¹) |
|---|---|---|---|---|---|---|---|---|---|---|---|---|
| | | | | | | | | | C | H | N | |
| 43 | [naphthyl-CH₃/OCH₃] | —CH₂CH₂OCH₃ | H | 1 | — | 2.5 | 3 | powder | 51.86 | 6.13 | 13.75 | 3,365 |
| | | | | | | | | | 51.77 | 6.00 | 13.72 | 3,200 |
| | | | | | | | | | | | | 1,620 |
| 44 | " | —CH₂CH₂OCH₃ | —C(CH₃)₃ | 1 | ½ H₂SO₃ | | 3 | powder | 51.47 | 6.65 | 11.54 | 3,370 |
| | | | | | | | | | 51.20 | 6.35 | 11.24 | 3,200 |
| | | | | | | | | | | | | 1,740 |
| | | | | | | | | | | | | 1,370 |
| 45 | " | —(CH₂)₃CH₃ | H | 1 | — | | 3 | powder | 54.43 | 6.55 | 13.80 | 3,375 |
| | | | | | | | | | 54.28 | 6.31 | 13.70 | 3,200 |
| | | | | | | | | | | | | 1,622 |
| 46 | " | —(CH₂)₃CH₃ | —C(CH₃)₃ | 1 | ½ H₂SO₃ | | 3 | powder | 53.63 | 7.00 | 11.58 | 3,380 |
| | | | | | | | | | 53.53 | 7.08 | 11.40 | 3,200 |
| | | | | | | | | | | | | 1,740 |
| | | | | | | | | | | | | 1,370 |
| 47 | " | —CH₂CH₂OCH₃ | H | 2 | — | | 3 | powder | 52.76 | 6.35 | 13.38 | 3,375 |
| | | | | | | | | | 52.47 | 6.01 | 13.09 | 3,180 |
| | | | | | | | | | | | | 1,620 |
| 48 | " | —CH₂CH₂OCH₃ | —C(CH₃)₃ | 2 | ½ H₂SO₃ | | 3 | powder | 52.24 | 6.82 | 11.28 | 3,380 |
| | | | | | | | | | 52.00 | 6.55 | 11.00 | 3,200 |
| | | | | | | | | | | | | 1,740 |
| | | | | | | | | | | | | 1,368 |

Having now fully described the invention, it will be apparent to one of ordinary skill in the art that many changes and modifications can be made thereto without departing from the spirit or scope of the invention as set forth herein.

What is claimed as new and intended to be covered by Letters Patent is:

1. N²-alkoxynaphthalenesulfonyl-L-argininamides having the formula:

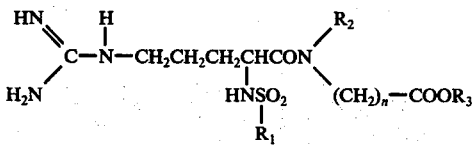

and the pharmaceutically acceptable salts thereof, wherein $R_1$ is a naphtyl substituted with at least one $C_1$–$C_5$ alkoxy; $R_2$ is $C_2$–$C_{10}$ alkyl or $C_2$–$C_{10}$ alkoxyalkyl; $R_3$ is hydrogen or $C_1$–$C_{10}$ alkyl; and $n$ is an integer of 1, 2 or 3.

2. The compound of claim 1, wherein $R_1$ is naphthyl substituted with one or two $C_1$–$C_3$ alkoxy groups; and $R_2$ is $C_2$–$C_6$ alkyl or $C_2$–$C_6$ alkoxyalkyl.

3. The compound of claim 1, wherein $R_1$ is selected from the group consisting of 5-methoxy-1-naphthyl, 6-methoxy-2-naphthyl, 7-methoxy-2-naphthyl, 4,6-dimethoxy-2-naphthyl, 6,7-dimethoxy-2-naphthyl and 6,7-diethoxy-2-naphthyl; $R_2$ is selected from the group consisting of propyl, butyl, isobutyl, pentyl, hexyl, octyl, 2-methoxyethyl, 2-ethoxyethyl and 3-methoxypropyl; and $R_3$ is selected from the group consisting of hydrogen, ethyl and tert-butyl.

4. The compound of claim 1, which is N²-(6,7-dimethoxy-2-naphthalenesulfonyl)-L-arginyl-N-(2-methoxyethyl)glycine.

5. The compound of claim 1, which is N²-(6,7-dimethoxy-2-naphthalensulfonyl)-L-arginyl-N-(2-ethoxyethyl)-β-alanine.

6. The compound of claim 1, which is N²-(4,6-dimethoxy-2-naphthalenesulfonnyl)-L-arginyl-N-(2-methoxyethyl)glycine.

7. The compound of claim 1, which is N²-(7-methoxy-2-naphthalenesulfonyl)-L-arginyl-N-(2-methoxyethyl)glycine.

8. The compound of claim 1, which is N²-(6,7-dimethoxy-2-naphthalenesulfonyl)-L-arginyl-N-butylglycine.

9. A method for inhibiting activity and suppressing activation of thrombin in vivo in mammals which comprises introducing into a living body a pharmaceutically effective amount of an N²-alkoxynaphthalenesulfonyl-L-argininamide having the formula:

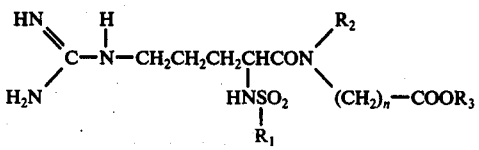

or the pharmaceutically acceptable salts thereof wherein $R_1$ is naphthyl substituted with at least one $C_1$–$C_5$ alkoxy; $R_2$ is $C_2$–$C_{10}$ alkyl or $C_2$–$C_{10}$ alkoxyalkyl, $R_3$ is hydrogen or $C_1$–$C_{10}$ alkyl; and $n$ is an integer of 1, 2 or 3.

10. A process for producing an N²-alkoxynaphthalenesulfonyl-L-argininamide having the formula (I):

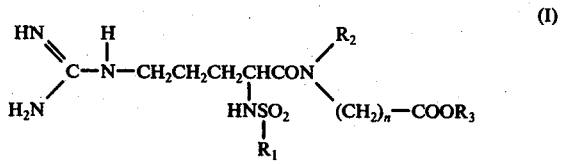

(I)

and the pharmaceutically acceptable salts thereof, wherein $R_1$ is alkoxynaphthyl wherein each alkoxy substituent contains 1–5 carbon atoms; $R_2$ is $C_2$–$C_{10}$ alkyl or $C_2$–$C_{10}$ alkoxyalkyl; $R_3$ is hydrogen or $C_1$–$C_{10}$ alkyl; and $n$ is an integer of 1, 2 or 3, which comprises reacting an N²-alkoxynaphthalenesulfonyl-L-arginyl halide having the formula (II):

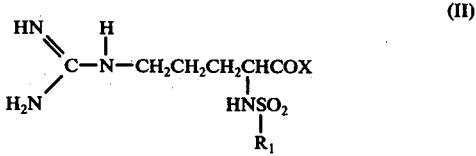

(II)

wherein $R_1$ is defined herein above, and X is halogen, with a secondary amine having the formula (III):

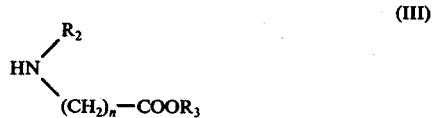

(III)

wherein $R_2$, $R_3$ and $n$ are defined herein above.

* * * * *

UNITED STATES PATENT AND TRADEMARK OFFICE
CERTIFICATE OF CORRECTION

PATENT NO. : 4,055,636
DATED : October 25, 1977
INVENTOR(S) : Okamoto, et al.

It is certified that error appears in the above-identified patent and that said Letters Patent are hereby corrected as shown below:

Abstract, line 1, "-arginiamides" should read -- -argininamides--

Column 1, line 34, "ester" should read --esters-- line 34, "amide" should read --amides--

Column 1, line 38, delete "or" and insert --of--

Column 1, line 58, "$C_1$-$C_5$ alkoxy" should read --$C_1$-$C_5$ alkoxy,--

Column 1, line 64, delete "into" and insert --in--

Column 2, line 25, delete "," (first instance) and insert --;--

Column 2, line 26, delete "of" (first instance) and insert --or--

Column 2, line 26, delete ";" and insert --.--

Column 2, line 51, "L-arginamides" should read --argininamides--

Column 3, line 24, "$N^2$(6,7-dimethoxy-2-naphthalenesulfonyl)-" should read --$N^2$-(6,7-dimethoxy-2-naphthalenesulfonyl)- --

UNITED STATES PATENT AND TRADEMARK OFFICE
CERTIFICATE OF CORRECTION

PATENT NO. : 4,055,636
DATED : October 25, 1977
INVENTOR(S) : Okamoto, et al.

It is certified that error appears in the above-identified patent and that said Letters Patent are hereby corrected as shown below:

Column 3, line 29, "-arginyll-" should read -- -arginyl- --

Column 5, line 5, delete "of" and insert -- or --

Column 5, line 11, delete "in" and insert -- the --

Column 5, line 57, "tertbutyox-" should read -- tert-butox- --

Column 6, line 58, "-argininamide" should read -- -argininamides --

Column 7, line 4, "$N^G$-substitited-$N^2$-substituted" should read -- $N^G$-substituted-$N^2$-substituted --

Column 7, line 13, "-alkoxynaphthalenesulfinyl-" should read -- -alkoxynaphthalenesulfonyl --

Column 7, line 33, "-arginamide" should read -- - argininamide --

Column 8, line 42, "agents" should read -- agent --

Column 8, line 64, delete "argininamide"

UNITED STATES PATENT AND TRADEMARK OFFICE
CERTIFICATE OF CORRECTION

PATENT NO. : 4,055,636

DATED : October 25, 1977

INVENTOR(S) : Okamoto, et al.

It is certified that error appears in the above-identified patent and that said Letters Patent are hereby corrected as shown below:

Column 9, line 10, "-argininamide" should read -- -argininamides --

Column 9, line 11, "forms" should read -- form --

Column 9, line 24, "an" should read -- a --

Column 9, line 68, "1,1000" should read -- 1,100 --

Column 10, line 1 "inhibotors" should read -- inhibitors --

Column 10, line 64, "ingreidnet" should read -- ingredient --

Column 11, line 14, "4,6-dimethoxy2-naph-" should read -- 4,6-dimethoxy-2-naph- --

Column 11, line 31, delete "1.742 $cm^{-1}$" and insert -- 1,742 $cm^{-1}$ --

Column 11, line 32, "$C_{25}H_{37}N_5O_8S \cdot C_{10}H_6 \ N2O_8S$" should read -- $C_{25}H_{37}N_5O_8S \cdot C_{10}H_6N_2O_8S$ --

Column 11, line 52, "-dimthoxy-" should read -- -dimethoxy- --

UNITED STATES PATENT AND TRADEMARK OFFICE
CERTIFICATE OF CORRECTION

PATENT NO. : 4,055,636
DATED : October 25, 1977
INVENTOR(S) : Okamoto, et al.

It is certified that error appears in the above-identified patent and that said Letters Patent are hereby corrected as shown below:

Column 12, line 2, "ethanoldiethyl" should read -- ethanol-diethyl --

Column 12, line 12, "-diemthoxy-" should read -- - dimethoxy --

Column 12, line 68, "-dimthoxy-" should read -- -dimethoxy- --

Column 14, line 14, "arginamides" should read -- argininamides --

Column 22, line fourth from bottom of table (Table 1) "54.36" should read -- 54.35 --

Column 25, line 18 (Claim 1, line 5) "naphtyl" should read -- naphthyl --

Column 25, line 42 (Claim 6, line 2), "-naphthalenesulfonnyl)-" should read -- -naphthalenesulfonyl)- --

Signed and Sealed this

Sixteenth Day of May 1978

[SEAL]

Attest:

RUTH C. MASON
Attesting Officer

LUTRELLE F. PARKER
Acting Commissioner of Patents and Trademarks

UNITED STATES PATENT AND TRADEMARK OFFICE
CERTIFICATE OF CORRECTION

PATENT NO. : 4,055,636
DATED : October 25, 1977
INVENTOR(S) : Shosuke Okamoto et al.

It is certified that error appears in the above—identified patent and that said Letters Patent is hereby corrected as shown below:

The term of this patent subsequent to January 3, 1995 has been disclaimed.

Signed and Sealed this

Fourteenth Day of October 1980

[SEAL]

Attest:

SIDNEY A. DIAMOND

Attesting Officer

Commissioner of Patents and Trademarks